United States Patent
Dufresne et al.

(10) Patent No.: US 10,199,198 B2
(45) Date of Patent: Feb. 5, 2019

(54) ELECTRON MICROSCOPE AND METHOD FOR TRANSMISSION ELECTRON MICROSCOPY IMAGING OF SAMPLE ARRAYS

(71) Applicant: Scienion AG, Berlin (DE)

(72) Inventors: Claude Dufresne, East Brunswick, NJ (US); Holger Eickhoff, Berlin (DE)

(73) Assignee: Scienion AG, Berlin (DE)

( * ) Notice: Subject to any disclaimer, the term of this patent is extended or adjusted under 35 U.S.C. 154(b) by 0 days.

(21) Appl. No.: 15/326,530

(22) PCT Filed: Jul. 17, 2014

(86) PCT No.: PCT/EP2014/001953
§ 371 (c)(1),
(2) Date: Jan. 16, 2017

(87) PCT Pub. No.: WO2016/008502
PCT Pub. Date: Jan. 21, 2016

(65) Prior Publication Data
US 2017/0207062 A1    Jul. 20, 2017

(51) Int. Cl.
*H01J 37/26*     (2006.01)
*G01N 1/31*      (2006.01)
(Continued)

(52) U.S. Cl.
CPC ............ *H01J 37/26* (2013.01); *G01N 1/2813* (2013.01); *G01N 1/30* (2013.01); *G01N 1/312* (2013.01);
(Continued)

(58) Field of Classification Search
CPC ........... H01J 2237/202; H01J 2237/204; H01J 37/26; G01N 1/2813; G01N 1/30; G01N 2001/282
See application file for complete search history.

(56) References Cited

U.S. PATENT DOCUMENTS 3,768,914 A * 10/1973 Kinney ................... G01N 1/31
356/244
8,754,384 B1    6/2014 Persoon et al.
(Continued)

FOREIGN PATENT DOCUMENTS

WO    2013109405 A1    7/2013
WO    2013109406 A1    7/2013

OTHER PUBLICATIONS

Castro-Hartmann et al., "The ArrayGrid: A methodology for applying multiple samples to a single TEM specimen grid", Ultramicroscopy, vol. 135, Dec. 1, 2013 (Dec. 1, 2013), pp. 105-112.
(Continued)

*Primary Examiner* — Wyatt Stoffa
(74) *Attorney, Agent, or Firm* — Caesar Rivise, PC

(57) ABSTRACT

A method of electron microscopy imaging of samples, using an electron microscope (100) having a microscope column (10) and a transfer device (11) with a grid carriage (12), comprises the steps of preparing multiple samples (1) on a single electron microscopy grid (2), including dispensing the samples (1) with a dispenser device (30) on distinct positions on the grid (2), introducing the grid (1) with the transfer device (11) into the microscope column (10), and electron microscopy imaging of the samples (1), wherein the preparing step includes holding the grid (2) on the grid carriage (12) of the transfer device (11) or on a grid holder device (20) provided at the electron microscope (100) and dispensing the samples (1) on the grid (2) while holding it on the grid carriage (12) or on the grid holder device (20). Furthermore, an electron microscope (100) for electron microscopy imaging of samples is described.

20 Claims, 3 Drawing Sheets

(51) Int. Cl.
*H01J 37/18* (2006.01)
*G01N 1/30* (2006.01)
*G01N 35/10* (2006.01)
*G01N 1/28* (2006.01)

(52) U.S. Cl.
CPC ........ *H01J 37/185* (2013.01); *G01N 35/1011* (2013.01); *G01N 2001/282* (2013.01); *H01J 2237/202* (2013.01); *H01J 2237/204* (2013.01); *H01J 2237/26* (2013.01)

(56) References Cited

U.S. PATENT DOCUMENTS

| | | | | |
|---|---|---|---|---|
| 2005/0107917 A1* | 5/2005 | Smith | ................. | B25J 15/0253 700/245 |
| 2011/0238225 A1* | 9/2011 | Tripathi | ................. | H01J 37/20 700/283 |
| 2012/0241607 A1* | 9/2012 | Bose | ................. | H01J 37/20 250/307 |
| 2012/0305769 A1* | 12/2012 | Yaguchi | ................. | H01J 37/20 250/310 |
| 2013/0014528 A1* | 1/2013 | Stabacinskiene | ................. | G01N 23/20033 62/129 |
| 2014/0360286 A1* | 12/2014 | Carragher | ................. | H01J 37/261 73/863.11 |
| 2015/0090899 A1* | 4/2015 | Carragher | ................. | G01N 1/30 250/428 |
| 2015/0243473 A1* | 8/2015 | Price | ................. | H01J 37/20 250/442.11 |
| 2017/0025250 A1* | 1/2017 | Carragher | ................. | G01N 1/30 |
| 2017/0213694 A1* | 7/2017 | Lihl | ................. | G01N 1/42 |

OTHER PUBLICATIONS

International Search Report for corresponding PCT/EP2014/001953 dated Mar. 17, 2015.

* cited by examiner

ELECTRON MICROSCOPE AND METHOD FOR TRANSMISSION ELECTRON MICROSCOPY IMAGING OF SAMPLE ARRAYS

CROSS-REFERENCE TO RELATED APPLICATIONS

This application is the U.S. National Phase Application of PCT/EP2014/00195, filed Jul. 17, 2014, the contents of which application is incorporated herein by reference in its entirety for all purposes.

BACKGROUND OF THE INVENTION

The invention relates to a method of transmission electron microscopy imaging of samples arranged on an electron microscopy grid. Furthermore, the invention relates to a transmission electron microscope, which is configured for transmission electron microscopy imaging of sample arrays. Applications of the invention are available in the imaging of multiple samples, including e. g. biological materials, like cellular macromolecules, crystals thereof, cellular components, or other biological particles, e. g. viruses, or non-biological materials, like nanoparticles.

Transmission electron microscopy (TEM) is a widely used method for imaging samples with an imaging resolution in the sub-nm range. The sample to be imaged is arranged on an electron microscopy grid, which typically comprises a circular mesh of metallic filaments covered with an electron transparent film, e. g. carbon film. Using a transfer device, the grid is loaded into an evacuated microscope column, wherein an imaging electron beam is directed through the sample and a transmission image is collected with a detector. Sample handling is a time consuming procedure, which represents a serious restriction if large quantities of samples are to be imaged, e. g. for high throughput imaging of biological samples.

In order to improve the TEM imaging of large quantities of samples, the creation of a sample array on the grid has been proposed in WO 2013/109405 A1. The sample array is deposited using an inkjet dispenser ejecting small droplets on the grid surface. A drive mechanism is used for positioning the grid relative to the inkjet dispenser. In order to remove excess liquid, which may comprise sample liquid or a liquid staining substance, the grid surface is provided with blotting material. The blotting material comprises e. g. porous membranes, which are capable of sucking liquids on the grid surface.

Due to the following disadvantages, the technique of WO 2013/109405 A1 has practical limitations. Firstly, the conventional grid handling requires a complex mechanical structure, e. g. for adjusting a grid holder relative to the inkjet dispenser. Loading the transfer device with the sample array grid may degrade the sample array, e. g. by an unintended bending of the grid. Furthermore, the conventional technique has a disadvantage in terms of a limited reliability of registering the samples for traceability. If the orientation of the sample array grid is changed during the loading to the transfer device, the sample identification can be lost.

The application of multiple biological samples on a single TEM grid also has been described by P. Castro-Hartmann et al. in "Ultramicroscopy", vol. 135, 2013, p. 105-112. The samples are deposited on the grid surface with a contact needle printer, followed by washing, staining and blotting steps. As a disadvantage of this technique, the contact needle printer requires TEM grids with high mechanical strength.

Providing small samples on a TEM grid without need for a blotting step is proposed in US 2011/0238225 A1. A liquid droplet sample is disposed with a first capillary on the grid surface, and excess liquid is removed from the droplet with a second capillary. Although this technique does not require blotting material on the grid surface, the conventional application of the capillaries results in limitations in terms of mechanically holding and precise position control of the capillaries. Furthermore, a sample identification for positive traceability is not possible with the device of US 2011/0238225 A1. Accordingly, this conventional technique is not applicable for high-throughput tasks, e. g. for removing liquid from a sample array on a TEM grid.

It is a first objective of the invention to provide an improved method of electron microscopy imaging of samples, being capable of avoiding disadvantages or limitations of conventional techniques. In particular, the disadvantages in terms of a cumbersome handling of sensitive grids, complex measures for blotting steps and/or limited registration reliability are to be avoided. It is another objective of the invention to provide an improved electron microscope, being capable of avoiding disadvantages of conventional electron microscopes and in particular facilitating the handling of grids with sample arrays.

These objectives are solved with a method and an electron microscope comprising the features of the invention.

DESCRIPTION OF THE INVENTION

According to a first general aspect of the invention, the above objective is solved by a method of electron microscopy imaging of samples, wherein an electron microscope, in particular a transmission electron microscope, TEM, comprising a microscope column and a transfer device with a grid carriage for introducing an electron microscopy grid into the microscope column is used. The electron microscopy imaging method comprises the steps of preparing multiple samples, in particular a sample array, on a single grid, wherein the samples are dispensed on distinct positions on the grid, introducing the grid on the grid carriage with the transfer device into the microscope column and collecting images of the samples on the grid. According to the invention, the samples are dispensed, while being held on the grid carriage. In particular, the grid is positioned on the grid carriage before depositing the samples on the surface of the grid.

The term "transfer device" refers to any component of the electron microscope being configured for moving a grid from a surrounding of the electron microscope, in particular at normal pressure (atmospheric pressure), to the evacuated inner space of the microscope column. Preferably, the transfer device is fixed to the microscope column. The term "grid carriage" refers to a movable component of the transfer device accommodating the grid, like a sliding support. The grid carriage can be permanently coupled with the transfer device, or it can be separable from the transfer device. The term "grid" refers to any sample substrate which is suitable for the electron microscopy imaging method applied, in particular transmission electron microscopy, in particular to any electron-transparent thin film, porous film and/or filament mesh being capable of carrying a sample to be imaged and being adapted for a support in the microscope column of the electron microscope. Preferably, the grid comprises a grid frame, e. g. with a circular or rectangular shape, surrounding a mesh of grid filaments or a porous film, e. g.

with a mesh or pore size depending on the grid type. With a mesh grid, the mesh size is in a range of e. g. 2 µm to 100 µm. With a pore grid, e. g. made of SiN, the pore size is in a range of e. g. 20 nm to 50 nm. Optionally, the grid may carry a thin film, e. g. made of carbon. Preferably, the grid is provided with a grid holder device, which generally comprises any component with a surface adapted for presenting a plurality of grids to a user or a picking device.

The term "dispenser device" refers to any droplet dispenser operated in a contactless mode for depositing droplets of a sample, a washing solution and/or a staining solution on the grid. Preferably, the dispenser device comprises at least one piezoelectric droplet dispenser. The piezoelectric droplet dispenser has a particular advantage in terms of the capability of controlling the velocity of the droplet(s) created. With a sensitive grid, the velocity of the droplet(s) can be reduced for avoiding a grid damage. Accordingly, the invention allows the use of thinner grids compared with conventional techniques thus improving the TEM imaging quality. With an embodiment using multiple piezoelectric droplet dispensers, each dispenser is separately controllable for depositing one or multiple droplets at each of the sample deposition positions on the grid surface. The droplet dispenser(s) preferably is/are supported by at least one translation stage, so that the droplet dispenser(s) is/are moveable relative to the grid carriage carrying the grid. Preferably, the plurality of samples, in particular an ordered sample array, can be created on the grid surface just before inserting the grid carriage into the transfer device or just before transferring the grid carriage carrying the grid into the microscope column. Advantageously, any complex handling steps, e. g. for moving a grid from a distant loading station to the transfer device are avoided, so that the risk of altering the sample, bending the grid or changing a registered orientation of the grid is minimized. The sample array created with the dispenser device comprises at least two samples, preferably an arrangement of at least 25 samples, in particular at least 100 samples or even more, e. g. a matrix arrangement with straight rows and columns of sample positions.

According to a second general aspect of the invention, the above objective is solved by an electron microscope, in particular a transmission electron microscope, which is adapted for electron microscopy imaging of samples and which comprises a microscope column and a transfer device with a grid carriage for introducing an electron microscopy grid into the microscope column. According to the invention, the electron microscope further is provided with a dispenser device, which is adapted for dispensing samples, in particular an ordered array of samples, onto the grid. The dispenser device is positioned adjacent to a microscope column such that the samples can be dispensed directly onto the grid, when the grid is held on the grid carriage of the transfer device. Preferably, the dispenser device is positioned with a support structure which is connected with the microscope column or arranged on a support table carrying the microscope column.

As an independent alternative of the invention, the preparing step may include holding the grid at the grid holder device, when the grid holder device is arranged adjacent to the electron microscope. The grid holder device, in particular including a grid holder card, is connected with a support table carrying the electron microscope column or directly with the electron microscope. According to this alternative aspect of the invention, the dispenser device is arranged such that the samples can be dispensed onto the grid when it is held at the grid holder device. With this feature of the invention, providing the above advantages for sample and grid handling and keeping a sample registration correspondingly can be facilitated.

According to a preferred embodiment of the invention, the samples are deposited on the grid when it is positioned on the grid carriage in the transfer device adjacent to an injection port of the microscope column for conducting the dispensing step. The transfer device has an access window where the grid carriage with the grid is exposed so that the samples can be dispensed to the grid in the transfer device. This embodiment can be used if the grid carriage is permanently coupled with the transfer device, or if the grid carriage is separable from the transfer device. Advantageously, the grid can be moved to a vacuum lock and introduced into the microscope column immediately after completing the preparing step. Any unintended bending of the grid or degradation of the samples can be avoided.

Alternatively, the samples are deposited onto the grid on the grid carriage when it is separated from the transfer device and the microscope column. This embodiment can be used if the grid carriage is separable from the transfer device. Immediately after the dispensing step, the grid carriage can be inserted into the transfer device, moved to the vacuum lock and introduced into the microscope column. Again, an unintended bending of the grid or degradation of the samples can be avoided.

According to a further preferred embodiment of the invention, the grid is provided with at least one identification feature which specifically identifies the grid and/or positions of the sample on the grid. With the one or more identification feature(s), the reliability of a grid and/or sample registration can be improved.

According to a first variant, the identification feature includes a dot code being arranged adjacent to the samples on the grid surface. Preferably, the dot code is created by depositing particles on the grid surface with the dispenser device. Preferably, the particles are made of an electron beam absorbing material, like e. g. carbon nanoparticles. According to a second variant, the identification feature includes a characteristic sample pattern formed by the samples on the grid surface. In other words, the samples can be deposited at predetermined positions such that an identification code is created by the samples. With this variant, the dot code is formed by the samples themselves. According to just a further variant, the identification feature includes a grid label, which is provided by the grid itself. Preferably, the grid label comprises a label mask made of at least one through-hole in the grid. A characteristic grid pattern, e. g. a pattern of through-holes, is formed by the grid label, wherein the grid pattern may comprise e. g. an alphanumeric identification (numbers and/or letters) and/or a code identification (dot and/or bar code). Preferably, the pattern of through-holes provides a label mask, which is formed in a frame portion of the grid. With preferred examples, through-holes having the shape of numbers and/or letters are made in the grid frame, so that the orientation of the grid and sample positions on the grid can be identified.

Advantageously, further procedures of the preparing step can be conducted using the dispenser device. According to a preferred variant, the preparing step includes a step of staining the samples with a liquid staining substance prior to TEM observation. Staining the samples comprises depositing electron dense atoms in or on the sample. It is used e. g. if the samples include organic, in particular biological materials. Preferably, if the sample comprises a biological material, the staining substance is adapted for selectively binding e. g. to desired cellular or protein regions. Otherwise, if nanoparticles with sufficient contrast are imaged, staining can be omitted. The staining substance comprises any substance being capable of increasing the contrast of the electron microscope image, e. g. a compound of heavy metals such as osmium, lead, uranium or gold (in immuno-gold labelling). Further examples of staining substances for negative staining include ammonium molybdate, uranyl acetate, uranyl formate, phosphotungstic acid, osmium tetroxide, osmium ferricyanide and auroglucothionate. These substances have advantages because they scatter electrons well and also adsorb to biological material well.

Preferably, the dispenser device is used for supplying the staining substance to the samples. According to an additional or alternative variant of the invention, the dispenser device can be used for removing excess liquid from the samples. The excess liquid comprises e. g. excess staining substance (if applied) or other excess liquid of the sample. Thus, according to a particularly preferred embodiment of the invention, the droplet dispenser(s) of the dispenser device, in particular the piezoelectric droplet dispenser(s), is/are used for removing the excess liquid at the locations of the samples. Advantageously, there is no need to provide blotting material on the grid surface or an additional mechanical holder for a second capillary for removing liquid as required with the conventional techniques. Some droplet dispenser(s) of the dispenser device can be used for depositing the samples, while other droplet dispenser(s) can be used for removing the excess liquid.

According to a further preferred embodiment, the inventive method may include an optical imaging of the grid on the grid carriage or on the grid holder device. Optical imaging includes collecting at least one optical image of the grid before or after dispensing the samples on the grid surface. Additionally or alternatively, the optical imaging includes collecting at least one optical image of the identification feature of the grid. Advantageously, the optical image(s) allow(s) a grid and/or sample registration. Thus, according to a particularly preferred embodiment of the invention, the preparing step is controlled using the optical image(s). For example, the preparing step is controlled such that the samples are dispensed in a central portion of the grid and/or with a predetermined orientation of the grid relative to the transfer device. Furthermore, the optical image(s) can be used for identifying locations of the sample on the grid. This allows a removal of the excess staining substance or other liquid even at the locations of the samples.

According to a further advantageous embodiment of the invention, the grid can be picked from the grid holder device, in particular the grid holder card for placing the grid on the transfer device. Picking the grid can be done with a picking device, so that the movement of the grid from the grid holder device to the transfer device can be conducted without a human intervention.

The inventive provision of the dispenser device coupled to the electron microscope facilitates high-throughput experiments. In particular for investigating biological samples, the exact conditions for obtaining significant TEM images cannot be predicted. The creation of the sample array on the grid at the transfer device (or with the alternative of the invention, at the grid holder device) facilitates a variation of sample conditions, like the buffer solution of the sample, the concentration of the sample, surfactants added to the sample, concentrations of the surfactants, the staining substance (if applied), concentrations of the staining substance, and/or surfactants added to the staining substance.

The grid holder device preferably comprises a planar grid holder card being adapted for carrying an array of grids. The grid holder card has an exposed plane surface where the grids can be picked with tweezers or the picking device. Preferably, the grid holder card has the size of a microscope slide. This facilitates the handling of the grids, e. g. for further pre-processing. According to a further preferred feature, at least one holder card label, like a bar code and/or another identification can be provided on the grid holder card. If the grid holder card has a self-adhesive surface holding the grids, the automatic handling of the grids without human intervention can be facilitated.

Preferably, the grid holder device is coupled with the electron microscope of the above second aspect of the invention. However, it is noted that the grid holder device with the planar grid holder card represents an independent third general aspect of the invention, which can be provided without the electron microscope of the above second aspect.

Further details and advantages of the invention are described in the following with reference to the attached drawings, which show in:

Features of preferred embodiments of the invention are described in the following with particular reference to the provision of a transmission electron microscope with a dispenser device and the preparation of a sample array on a grid just before introducing the grid into the electron microscope. Details of the electron microscope and the dispenser device as such and methods of operating thereof are not described as far as they are known from conventional electron microscopes or dispenser devices. Furthermore, exemplary reference is made to the use of a translation device having a sliding grid carriage for introducing a grid into the microscope column of the electron microscope, wherein the grid carriage is permanently coupled with the transfer device. The implementation of the invention is not restricted to the use of this type of transfer device, but rather possible with other types of transfer devices, e. g. having a removable grid carriage.

Figure 1:
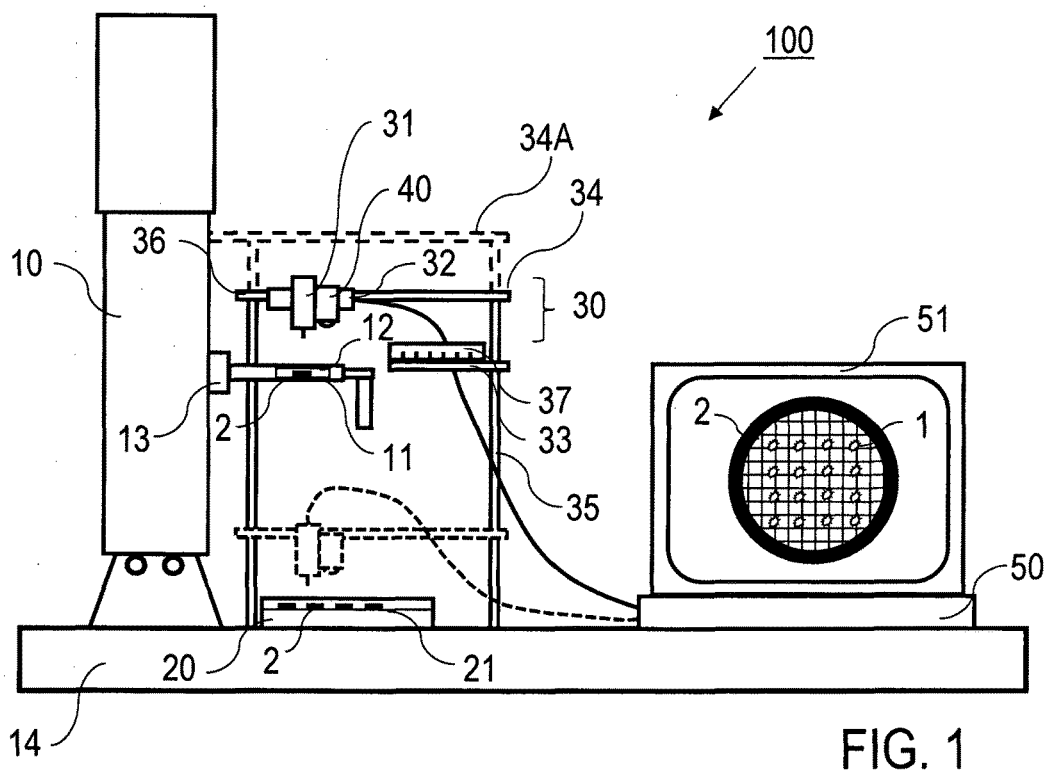
FIG. 1: features of preferred embodiments of an electron microscope according to the invention.

FIG. 1 represents a schematic illustration of the electron microscope 100 having a microscope column 10 comprising a transfer device 11 with a grid carriage 12, a grid holder device 20, a dispenser device 30, an optical imaging device 40 and a control device 50 with a display 51. The electron 100 further includes a support table 14 and additional components, like a power supply and a vacuum equipment (not shown in FIG. 1). As an example, an electron microscope Tecnai G2 (manufacturer: FEI) is used for implementing the invention.

Figure 2:
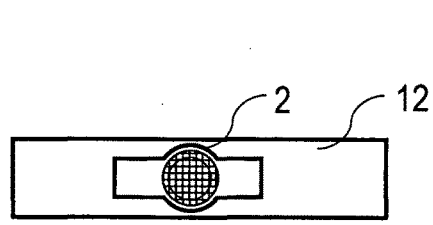
FIG. 2: a schematic partial plan view of a transfer device used according to the invention.

The transfer device 11 includes the sliding grid carriage 12 (exemplary plan view shown in FIG. 2) and a vacuum lock 13 providing an injection port of the microscope column 10. The transfer device 11 is adapted for accommodating and shifting the grid carriage 12 with the grid 2 through the vacuum lock 13 and further into the beam path of the microscope column 10. The grid carriage 12 is shifted manually or using a motion drive. The transfer device 11 may have a removable grid carriage, like e. g. a sample holder of the manufacturer Gatan, USA.

Figure 5:
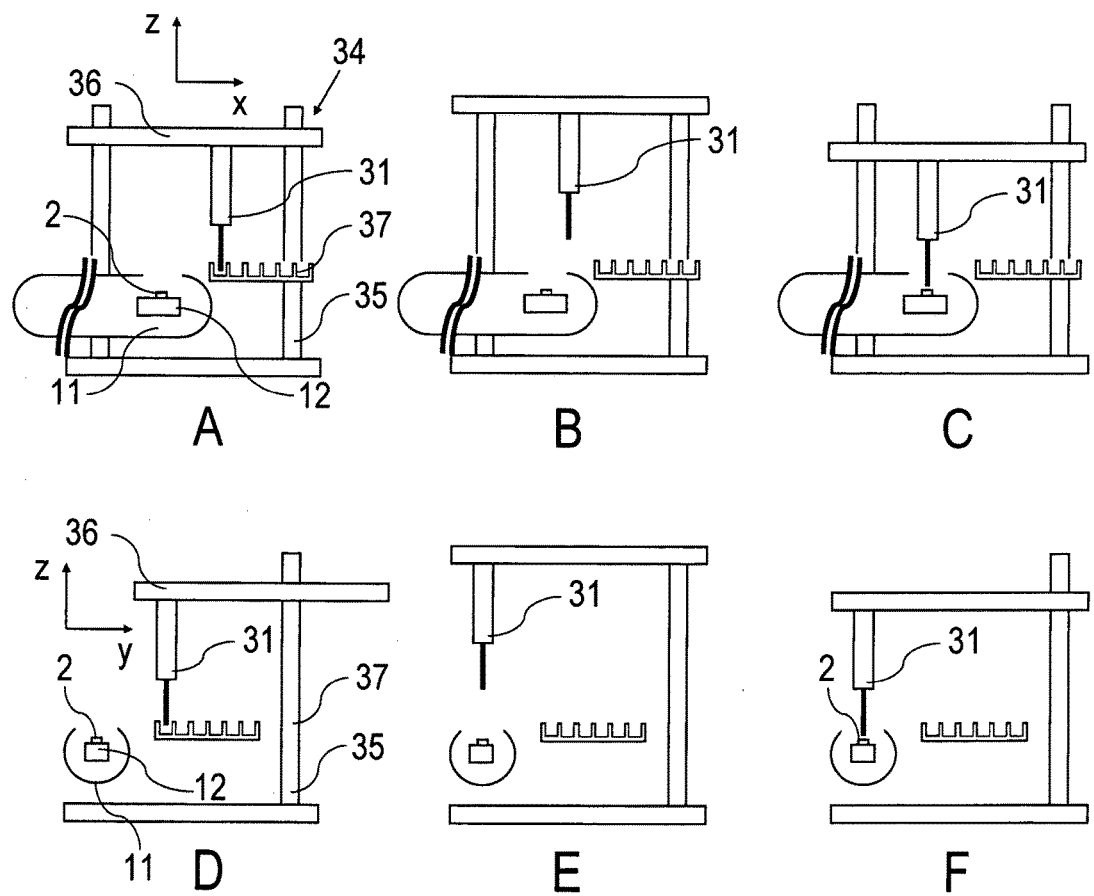
FIG. 5: schematic illustrations of depositing samples from a sample plate onto a grid.

The dispenser device 30 includes a piezoelectric droplet dispenser 31, a translation stage 32 and a sample plate carrier 33. The translation stage 32 and the sample plate carrier 33 have a fixed position relative to the microscope column 10. These components are connected with a support structure 34 comprising multiple vertical support rods 35 and at least one horizontal support beam 36 for moving the translation stage 32. The support structure 34 is positioned e. g. on the support table 14 as shown with drawn lines in FIG. 1. Alternatively, the support structure 34 can be directly connected with the microscope column 10 as shown at 34A with dashed lines in FIG. 1. Further exemplary features of the support structure 34 are illustrated in FIG. 5. With a preferred example, the dispenser device 30 comprises the apparatus sciFLEXARRAYER (manufacturer: Scienion AG, Germany).

The sample plate carrier 33 provides a support e. g. for a microtiter plate 37, wherein samples e. g. with varying buffer solutions or surfactants and optionally washing and/or staining solutions are arranged in the wells of the microtiter plate 37. Preferably, the sample plate carrier 33 is coupled with the support structure 34, e. g. with one of the vertical support rods 35.

The optical imaging device 40 comprises a CCD camera, which is mechanically connected with the piezoelectric droplet dispenser 31, the translation stage 32 or the support structure 34. The optical imaging device 40 is arranged for collecting an optical image of the sliding carriage 12 including the grid 2.

Figure 3:
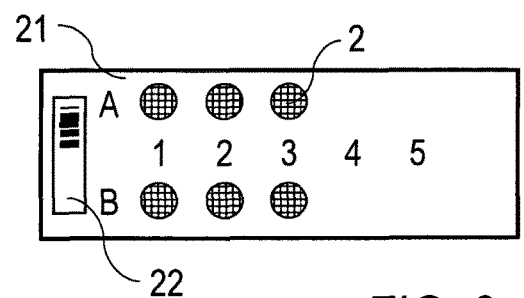
FIG. 3: a schematic plan view of a grid holder card.

The grid holder device 20 comprises a grid holder card 21 (exemplary plan view shown in FIG. 3), which carries a plurality of grids 2. With the illustrated preferred example, the grids 2 are provided with a matrix arrangement with two rows A and B and five columns 1 to 5. The number/letter of the columns and rows provides an identification of the grids 2, which can be assigned to an identification feature of the grids 2. The grid comprise e. g. pore grids made of nanoporous amorphous SiN films with a 100 µm thick frame, a 500 µm*500 µm window, an average pore diameter of 30 nm and a porosity of about 25% (manufacturer SiMPore, USA).

Figure 4:
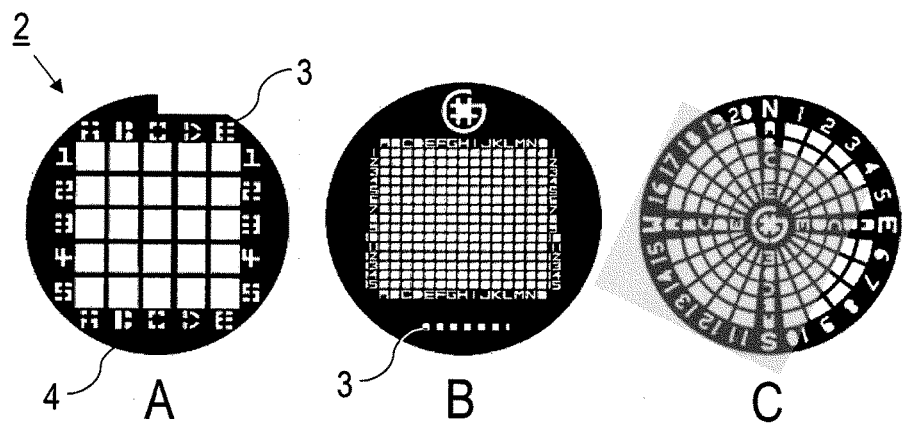
FIG. 4: illustrations of grids with grid labels.

FIGS. 4A to 4C illustrate examples of identification features of the grid 2, wherein the identification features comprise grid labels 3, which are formed as through-holes in a circumferential portion of the grid 2 (grid frame 4) and/or as a dot code (see FIG. 4B). The identification features allow a traceability of grids and grid recognition inside or outside the microscope.

FIGS. 5A to 5F illustrate temporal phases of dispensing the samples onto the grid 2 with schematic front views (FIGS. 5A to 5C, see also FIG. 1) and schematic side views (FIGS. 5D to 5F) of the transfer device 11 and the support structure 34. According to FIG. 5A, the transfer device 11 (shown in part) includes the grid carriage 12 with the grid 2. The support structure 34 includes two vertical support rods 35 extending in a vertical direction (z-direction) and two horizontal support beams 36. The horizontal support beams 36 provide a frame extending in horizontal directions (x-y-directions) perpendicular to the vertical support rods 35 and being movable with translation stages (not shown) in the vertical (z) and one (y) of the horizontal directions. The droplet dispenser 31 is coupled to one of the horizontal support beams 36. It is movable with a further translation stage (not shown, see translation stage 32 in FIG. 1) in the other one (x) of the horizontal directions. A microtiter plate 37 is coupled via a plate carrier (not shown) with one of the vertical support rods 35.

With a preferred embodiment of the invention, the electron microscopy imaging of the samples on the grid 2 is conducted with the following steps. Firstly, grids 2 are provided in the grid holder device 20 (see FIG. 1). One particular grid 2 is selected in dependency on the number and size of samples to be arranged as an array on the grid surface. The selected grid 2 is positioned on the sliding carriage 12 of the transfer device 11. The grid 2 is moved to the sliding carriage 12 using tweezers or a picking device (not shown).

Subsequently, with the embodiment of FIG. 5, the samples are dispensed on distinct positions on the grid 2 when it is held at the transfer device 11. The samples are taken with the piezoelectric droplet dispenser 31 from the microtiter plate 37 and deposited on the grid 2. The dispenser device 30 and the translation stages of the support structure 34 are controlled with the control device 50 in dependency on an optical image collected with the optical imaging device 40 and presented for monitoring purposes on the display 51 (see FIG. 1).

According to FIGS. 5A and 5D, the samples are aspirated from the microtiter plate 37 on the plate carrier. To this end, the piezoelectric droplet dispenser 31 is moved into one of the wells of the microtiter plate 37 and operated for accommodating the sample liquid. Subsequently, the piezoelectric droplet dispenser 31 is lifted in the vertical direction and moved to the transfer device 11, as shown in FIGS. 5B and 5E. Finally, the sample is dispensed onto the grid 2. According to FIGS. 5C and 5F, the piezoelectric droplet dispenser 31 is lowered towards the transfer device 11.

Figure 6:
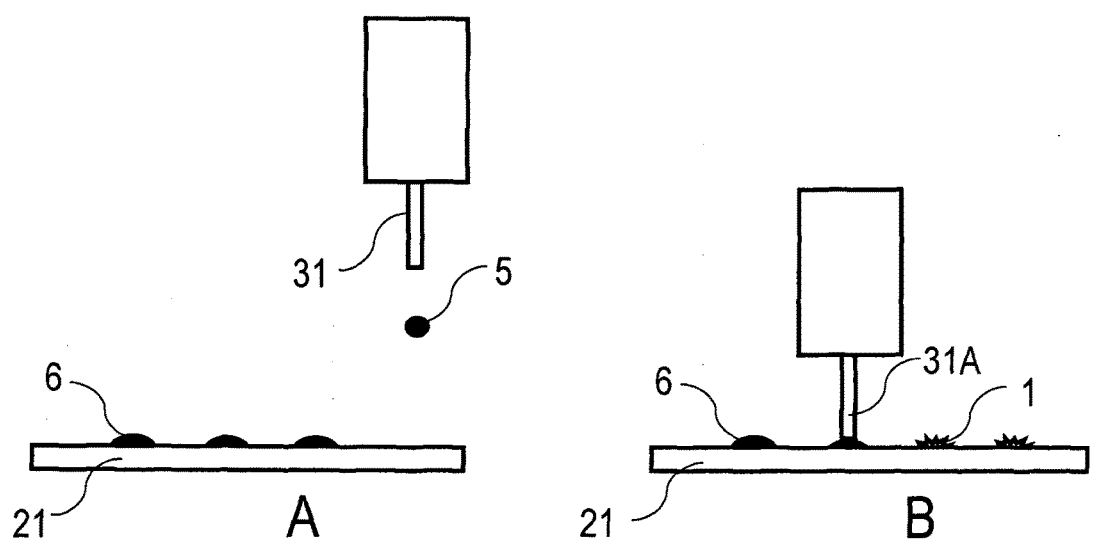
FIG. 6: further schematic illustrations of depositing samples onto a grid (FIG. 6A) and removing excess liquid from the samples (FIG. 6B).

FIG. 6A schematically illustrates the creation of flying droplets 5 and the deposition on the grid 2 using the piezoelectric droplet dispenser 31. With the translation stage 32 (see FIG. 1), the piezoelectric droplet dispenser 31 is adjusted relative to the grid 2 such that the liquid droplets 6 are deposited at the distinct positions on the grid surface.

Subsequently, the dispenser device 30, e. g. another dispenser 31A thereof is used for removing excess liquid from the deposited droplets 6, so that the samples 1 to be imaged remain on the grid surface (FIG. 6B). If the samples are to be stained, the staining substance is supplied and excess staining substance is removed with the dispenser device 30, e. g. just another piezoelectric droplet dispenser thereof.

Finally, the grid 2 with the sample array is moved through the injection port into the microscope column 10. Transmission electron microscopy images of the samples 1 are collected as it is known from conventional transmission electron microscopy. The electron microscopy images are assigned to specific samples using the identification features 3 of the sample grids 2.

The features of the invention disclosed in the above description, the drawings and the claims can be of importance individually or in combination for the realisation of the invention in its different embodiments.

The invention claimed is:
1. A method of electron microscopy imaging of samples, using an electron microscope having a microscope column and a transfer device with a horizontally oriented grid carriage, comprising:
preparing multiple samples on a single electron microscopy grid, including dispensing the samples with a dispenser device on distinct positions on the grid, introducing the grid with the grid carriage of the transfer device into the microscope column, the horizontally oriented grid carriage being configured for supporting and moving the grid from a surrounding of the electron microscope at atmospheric pressure to an evacuated inner space of the microscope column, and electron microscopy imaging of the samples on the grid supported by the grid carriage during the imaging, wherein the preparing step includes holding the grid on the horizontally oriented grid carriage of the transfer device and dispensing the samples on the grid while holding the grid on the horizontally oriented grid carriage.

2. The method according to claim 1, wherein, for dispensing the samples onto the grid on the grid carriage, the grid is provided on the grid carriage being inserted in the transfer device adjacent to an input port of the microscope column, or the grid is provided on the grid carriage being separated from the transfer device.

3. The method according to claim 1, wherein the grid has at least one identification feature, which identifies at least one of the grid itself and positions of the samples on the grid.

4. The method according to claim 3, wherein the identification feature includes at least one of a dot code arranged adjacent to the samples, a characteristic sample pattern formed by the samples, and a characteristic grid pattern formed by a grid label.

5. The method according to claim 4, wherein at least one of the dot code and the characteristic sample pattern is deposited on the grid after arranging the grid on the grid carriage.

6. The method according to claim 1, wherein the step of dispensing the samples onto the grid includes varying at least one of buffer solutions of the samples, concentrations of the samples, surfactants added to the samples, and concentrations of the surfactants.

7. The method according to claim 1, wherein the step of preparing the samples on the grid includes at least one of staining the samples with a staining substance, wherein the dispenser device is used for supplying the staining substance to the samples, and removing excess liquid with the dispenser device from the samples.

8. The method according to claim 7, wherein the step of staining the samples on the grid includes varying at least one of the staining substance, surfactants added to the staining substance and concentrations of the staining substance.

9. The method according to claim 1, including a step of optical imaging the grid on the grid carriage for collecting at least one optical image of the grid or an identification feature thereof.

10. The method according to claim 9, wherein the preparing step is controlled using the optical image such that the samples are dispensed in at least one of a central portion of the grid and a predetermined orientation of the grid relative to the grid carriage.

11. The method according to claim 9, wherein the preparing step includes determining locations of the samples using the optical image, and removing the excess liquid at the locations of the samples.

12. The method according to claim 1, the introducing step including introducing the grid with the grid carriage of the transfer device through a vacuum lock of the transfer device into the microscope column, the vacuum lock providing an injection port into the evacuated inner space of the microscope column for the horizontally oriented grid carriage of the transfer device to introduce the electron microscopy grid into the evacuated inner space of the microscope column for electron microscopy imaging of the samples on the grid that is supported by the grid carriage.

13. An electron microscope for electron microscopy imaging of samples, comprising a microscope column having a transfer device with a horizontally oriented grid carriage, wherein the horizontally oriented grid carriage of the transfer device is configured for supporting and introducing an electron microscopy grid from a surrounding of the electron microscope at atmospheric pressure into an evacuated inner space of the microscope column for electron microscopy imaging of the samples on the grid supported by the grid carriage, and a dispenser device arranged adjacent to the microscope column, such that the dispenser device is capable of dispensing the samples onto the grid while the grid is held on the horizontally oriented grid carriage of the transfer device.

14. The electron microscope according to claim 13, wherein the dispenser device is arranged for dispensing the samples onto the grid on the grid carriage being coupled with the transfer device adjacent to an input port of the microscope column.

15. The electron microscope according to claim 14, wherein the dispenser device is coupled with the microscope column.

16. The electron microscope according to claim 13, wherein the dispenser device is arranged for dispensing the samples onto the grid on the grid carriage when the grid carriage is positioned with a distance from the transfer device.

17. The electron microscope according to claim 13, wherein the dispenser device comprises at least one piezoelectric dispenser.

18. The electron microscope according to claim 13, further comprising a sample plate carrier coupled with the dispenser device.

19. The electron microscope according to claim 13, further comprising an optical imaging device being arranged for collecting at least one optical image of the grid arranged at the transfer device.

20. The electron microscope according to claim 13, the transfer device further including a vacuum lock providing an injection port into the evacuated inner space of the microscope column for the horizontally oriented grid carriage of the transfer device to introduce the electron microscopy grid into the evacuated inner space of the microscope column for electron microscopy imaging of the samples on the grid that is supported by the grid carriage.

* * * * *